United States Patent
Barron et al.

(10) Patent No.: US 7,115,764 B2
(45) Date of Patent: Oct. 3, 2006

(54) MECHANICAL SHEAR BASED SYNTHESIS OF ALUMOXANE NANOPARTICLES

(75) Inventors: Andrew R. Barron, Houston, TX (US); Naureen Shahid, Houston, TX (US)

(73) Assignee: Wm. Marsh Rice University, Houston, TX (US)

( * ) Notice: Subject to any disclaimer, the term of this patent is extended or adjusted under 35 U.S.C. 154(b) by 129 days.

(21) Appl. No.: 10/636,174

(22) Filed: Aug. 7, 2003

(65) Prior Publication Data

US 2004/0110976 A1    Jun. 10, 2004

Related U.S. Application Data

(60) Provisional application No. 60/401,535, filed on Aug. 7, 2002.

(51) Int. Cl.
    C07F 5/06 (2006.01)
(52) U.S. Cl. .................. 556/178; 556/179; 428/402; 428/403
(58) Field of Classification Search .............. 556/179, 556/178; 428/402, 403
    See application file for complete search history.

(56) References Cited

U.S. PATENT DOCUMENTS

| | | | |
|---|---|---|---|
| 4,496,714 | A | 1/1985 | Murata et al. |
| 4,676,928 | A | 6/1987 | Leach et al. |
| 4,952,634 | A | 8/1990 | Grossman |
| 5,212,261 | A | 5/1993 | Stierman |
| 5,418,298 | A | 5/1995 | Laine et al. |
| 5,593,781 | A * | 1/1997 | Nass et al. ............ 428/403 |
| 6,207,130 | B1 | 3/2001 | Kareiva et al. |
| 6,322,890 | B1 * | 11/2001 | Barron et al. ........... 428/402 |
| 6,369,183 | B1 | 4/2002 | Cook et al. |
| 6,770,773 | B1 | 8/2004 | Rose et al. |

FOREIGN PATENT DOCUMENTS

EP           0576695        6/1992

OTHER PUBLICATIONS

Callender et al., "Aqueous synthesis of water-soluble alumoxane: environmentally benign precursors to alumina and aluminum based ceramics", Chem. Mater., 9, 2418-2433(1977).*
Callender et al., Chem. Matter., 9, 2418-2433(1997).*
Landry et al., J. Mater. Chem., 5(2), 331-341 (1995).*
Kareiva et al. Chem. Mater., 8, 2331-2340(1996).*
Zaspalis et al., *Synthesis and Characterization of Primary Alumina, Titania and Binary Membranes*, Journal of Materials Science 27 (1992) pp. 1023-1035.
Yoldas, *Alumina Gels that Form Porous Transparent $Al_2Oihd\ 3$*, Journal of Materials Science 10(1975) pp. 1856-1860.
Low et al., *Synthesis and Properties of Spodumene-modified Mullite Ceramics formed by Sol-gel Processing*, Journal of Materials Science Letters 16 (1997) pp. 982-984.
Nikolic et al., *Alumina Strengthening by Silica Sol-get Coating*, Thin Solid Films 295 (1997) pp. 101-103.
Rezgui et al., *Chemistry of Sol-Gel Synthesis of Aluminum Oxides with in Situ water Formation: Control of the Morphology and Texture*, Chem Mater (1994) 6, pp. 2390-2397.
Serna et al., *Division S-9—Sole Mineralogy*, Soil Sci. Soc. Am. Journal, vol. 41 (1997) pp. 1009-1013.
Kingery et al., *Introduction to Ceramics* Wiley-Interscience Publication, 1960.
Landry et al., *From Minerals to Materials: Synthesis of Alumoxanes from the Reaction of Boehmite with Carboxylic acids*, Journal of Mater. Chem., 1995, 5(2) pp. 331-341.
Lao et al., *Microporous Inorganic Membranes: Preparation by the Sol-gel Process and Characterization of Unsupported Composite Membranes of Alumina and Polyoxoaluminium Pillard Montmorillonite*, Journal of Materials Science Letters 13 (1994) pp. 895-897.
Sirkar, *New Membranes Materials and Process for Sepatation*, Published by American Institute of Chemical Engineers, 1988.
Kareiva et al., *Carboxylate-Substituted Alumoxanes as Processable Precursors to Transition Metal-Aluminum and Lanthanide-Aluminum Mixed-Metal Oxides: Atomic Scale Mixing via a New Transmetalation Reaction*, Chemistry of Materials vol. 8, No. 9, pp. 2331-2340.
Wilson et al., *The Porosity of Aluminum Oxide Phases Derived from Well-Crystallized Boehmite: Correlated Electron Microscope, Adsorption, and Porosimetry Studies*, Journal of Colloid and Interface Science, vol. 82, No. 2, Aug. 1981 (pp. 507-517).
Adkins, *The Selective Activation of Alumina for Decarboxylation or for Dehydration*, Selective Activation of Alimina pp. 2175-2186.
Courtright, *Engineering Property Limitations of Structural Ceramics and Ceramic Composites Above 1600°C*, Ceramic Engineering Science Proc. 12(9-10) pp. 1725-1744 (1991).
Elaloui et al., *Influence of the Sol-Gel Processing Method on the Structure and the Porous Texture of Nondoped Aluminas*, Journal of Catalysis 166, pp. 340-346 ( 1997).

(Continued)

*Primary Examiner*—Ling-Sui Choi
(74) *Attorney, Agent, or Firm*—Conley Rose, P.C.

(57) ABSTRACT

A method for forming carboxylate-alumoxane nanoparticles comprises subjecting a mixture comprising boehmite and carboxylic acid to mechanical shear. The method can be carried out at a temperature above ambient and preferably a temperature greater than 80° C., and can be carried out in the absence of a liquid phase.

14 Claims, 4 Drawing Sheets

OTHER PUBLICATIONS

Nagami, *Sol-gel Preparation of SiO₂ Glasses Containing Al₂O₃ or ZrO₂*, Journal of Non-Crystalline Solids 178 (1994) pp. 320-326.

Okubo et al., *Preparation of y-alumina Thin Membrane by Sol-gel Processing and its Characterization by Gas Permeation*, Journal of Materials Science 25 (1990) pp. 4822-4827.

Rezgui et al., *Control of Magnesia-alumina Properties by Acetic Acid in Sol-gel Synthesis*, Journal of Non-Crystalline Solids 210 (1997) pp. 287-297.

Shelleman et al., *Alpha Alumina Transformation in Seeded Boehmite Gels*, Journal of Non-Chrystalline Solids 82 (19986) pp. 277-285.

Lin et al., *Thermal Stability and its Improvement of the Alumina Membrane Top-layers Prepared by Sol-gel Methods*, Journal of Materials Science, 26 (1991) pp. 715-720.

Michalske et al., *Strength and Toughness of Continuous-Alumina-Fiber-Reinforced Glass-Matrix Composites*, Journal of American Ceramic Society, vol. 71, No. 9 pp. 725-731 (1988).

Anderson et al., *Titania and Alumina Ceramic Membranes*, Journal of Membrane Science, 39 (1988) pp. 243-258.

Baltus, *Characterization of the Pore Area Distribution in Porous Membranes using Transport Measurements*, Journal of Membrane Science, 123 (1197) pp. 165-184.

Furneaux et al., *The Formation of Controlled-porosity Membranes from Anodically Oxidized Aluminum*, Nature vol. 337, Jan. 12, 1989 (pp.147-149).

Kim et al., *Hydraulic and Surface Characteristics of Membranes with Parallel Cylindrical Pores*, Journal of Membrane Science, 123 (1997) pp. 303-314.

C. landry, et al; *Siloxy-Substituted Alumoxanes: Synehesis from Polydialkylsiloxanes and Trimethylaluminium, and Application as Aluminosilicate Precursors*; J. Mater. Chem. 1993; (pp. 597-6020).

H. Schmidt and H. Krug, "Sol-gel-based inorganic-organic composite materials", ACS Symp. Se. 572, No. Inorganic and Organometallic Polymers 11, 183-194, (1994).

Y. Kimura, S. Tanimoto, H. Yamane, T. Kitao, *"Coordination Structure of the Aluminium Atoms of Poly (Methylaloxane), Poly (Isopropoxylaloxane) and Poly [Acyloxy Aloxane]"*, Polyhedron, vol. 9, No. 2/3, 371-376, (1990).

Harry S. Katz, et al. *Handbook of Fillers and Reinforcements for Plastics*, Van Nostrand Reinhold Company, 1978 (49p.).

Bryan Ellis, *Chemistry and Technology of Epoxy Resins*, Blackie Academic & Professional, an Imprint of Chapman & Hall, (80p.).

R. Kasemann, H. Schmidt; *Coatings for Mechanical and Chemical Protection based on Organic-Inorganic Sol-Gel Nanocomposites*; New Journal of Chemistry, vol. 18, No. 10-1994; (pp.1117-1123).

C. Vogelson, et al; *Inorganic-Organic Hybrid and Composite Materials Using Carboxylate-Alumoxanes*; World Ceramics Congress, Jun. 14-19, 1998; (pp. 499-506).

S. Pasynkiewicz, *Alumoxanes: Synthesis, Structures, Complexes and Reactions*, Polyhedron, vol. 9, No. 2/3, 1990 (25p.).

K. Nakamae, et al; *Studies on Mechanical Properties of Polymer Comnposites by X-ray diffraction: 3. Mechanism of Stress Transmission in Particulate Epoxy Composite by X-ray Diffraction*; Polymer, 1992, vo..33, No. 13; (pp.2720-2724).

H. Jullien, et al. *The Microwave Reaction of Phenyl Glycidyl Ether with Aniline on Inorganic Supports: a Model for the Microwave Crosslinking of Epoxy Resins*;Polymer, vol. 37, No. 15; 1996; (pp.3319-3330).

H. Schmidt, et al; *Chemistry and Applications of Inorganic-Organic Polymers*; Mat. Res. Soc. -Symp. Prac. vol. 73; 1986; (pp.739-750).

J. Dewit, et al; *Evaluation of Coatings - A Total System Approach*; Materials Science Forum, vol. 247 (1997) (pp. 69-82).

Jacqueline I. Kroschwitz, et al., *Encyclopedia of Polymer Science and Engineering*, vol. 6, *Emulsion Polymerization to Fibers, Manufacture*, A Wiley-Interscience Publication, 1985, (66p.).

K. Andriano, et al; *Synthesis of New Polymers with Inorganic Chains of Molecules*; Journal of Polymer science, vol. XXX, 1958 (pp. 513-524).

G. Whiteside, et al; Articles; *Molecular Self-Assembly and Nanochemistry: A chemical Strategy for the Synthesis of Nanostructures*; Science, vol. 254, Nov. 1991; (pp. 1312-1319).

Malcolm P. Stevens, *Polymer Chemistry, An Introduction*, Oxford University Press, 1990 (9 p.).

Christopher C. Landry, et al., *From Minerals to Materials: Synthesis of Alumoxanes from the Reaction of Boehmite with Carboxylic Acids*, J. Mater, Chem., 5(2), 331-341 (1995).

A. Apblett, et al; *Synthesis and Characterization of Triethylsiloxy-Suybstituted Alumoxanes: Their Structural Relationship to the Minerals Boehmite and Diaspore*; American Chemical Society; 1992; (pp. 167-181).

Y. Koide, et al; $[Al_5(Bu)_{s(u5}O)_2((\mu\text{-}OH)_2(\mu O_2i \text{ CPH})_2]$: *A Model for the Interaction of Carboxylic Acids with Boehmite*; American Chemical Society 1995; (pp. 4025-4029).

A. Macinnes, et al; *Chemical Vapor Deposition of Gallium Sulfide: Phase Control by Molecular Design*; American Chemical society, 1993; (pp. 1344-1351).

J. M. G. Cowie, Professor of Chemistry, University of Stirling, *Polymers: Chemistry and Physics of Modern Materials*, Intertext Books, (13 p.).

Tomlinson et al., *Thermal Conductivity of Epoxy resin-Aluminium (0 to 50%); and Diavalent Chromium in Alkaline Earth Silicate Systems*; J. of Materials Science, 12 1689-1690 (1977).

H. Schmidt et al., *Inorganic-Organic Hybrid Coatings for Metal and Glass Surfaces*, American Chemical Society 1995 (pp. 331-347).

Chemical Abstracts, vol. 111, No. 24, Dec. 11, 1989, abstract No. 218306m, Uhlhorn, R.J.R.: High permselectivities of microporous silica modified gamma-alumina membranes: XP000181419.

Cinibulk, *Microstructure and Mechanical Behavior of an Hibonite Interphase in Aluminia-Based Composites*, Ceramic Eng. & Science Proceedings of the 19th Annual Conference and Exhibition on Composites, adv. Ceramics, Materials, and Structures Part B. Jan. 8-12, 1995, vol. 16 No. 5.

Cinibulk, *Magnetoplumbite Compounds as a Fiber Coating in Oxide/Oxide Composites*, Ceramic Eng. And Science Proc. 18th Annual Conference, vol. 15, No. 15 Sept.- Oct. 1994, pp. 721-728.

Bhave et al., *MembraneMaterialsandProcessRemoval of Oily Contaminants in Wastewater with Microporous Alumina Membranes*, pp. 19-27 (1988).

Guizard et al., *ChemicalProcessingofCeramics,Ceramic Membrane Processing*, pp. 501-553, (1994).

Cinibulk, *Thermal Stability of Some Hexaluminates at 1400°C*, Journal of Materal Science Letters 14 (1995) pp. 651-654.

Cinibulk, *Magnetoplumbite Compounds as a Fiber Coating in Oxide/Oxide Composites*, Ceramic Eng. And Science Proc. 18th Annual Conference, vol. 15, No. 15 Sept.- Oct. 1994, pp. 721-728.

Collongues et al., *Magnetoplumbite-Related Oxides*, Annual Rev. Matter. Sci. (1990) 20, pp. 51-82.

Defriend et al., *A Simple Approach to Hierarchical Ceramic Ultrafiltration Membranes*, Journal of Membrane Science 212 (2003) pp. 29-38.

Defriend et al., *A Flexible Route to High Strength a-alumina and Aluminate Spheres*, Journal of Materials Science 38 (2003) pp. 2673-2678.

Hay et al., *Sol-Gel Coatings on Continuous Ceramic Fibers*, Ceramic Eng. Sci. Proc. 11 [9-10] pp. 1526-1538 (1990).

Mauch, "Divalent Chromium in Alkaline Earth Silicate Systems", J. of Materials Science, 12, 1690-1691 (1977).

\* cited by examiner 4-hydroxybenzoic acid 4-aminobenzoic acid dimethylolpropionic acid
(2,2-bis-(hydroxymethyl)propionic acid)

diphenolic acid
(4,4-bis(4-hydroxyphenyl)valeric acid)

6-aminohexanoic acid
(6-aminocaproic acid)

lysine
(2,6-diaminohexanoic)

+ HO₂CR | - H₂O

US 7,115,764 B2

MECHANICAL SHEAR BASED SYNTHESIS OF ALUMOXANE NANOPARTICLES

CROSS-REFERENCE TO RELATED APPLICATIONS

This application claims the benefit of U.S. provisional patent application Ser. No. 60/401,535, filed Aug. 7, 2002, which is incorporated herein by reference in its entirety. The teachings of U.S. Pat. No. 6,369,183 B1, filed Aug. 13, 1998 and entitled "Method and Materials for Fabrication of Alumoxane Polymers," and U.S. Pat. No. 6,322,890 B1, filed Mar. 26, 1999 and entitled "Supra-Molecular Alkylalumoxanes," are also incorporated by reference herein in their entireties.

STATEMENT REGARDING FEDERALLY SPONSORED RESEARCH OR DEVELOPMENT

This invention was made with partial support under NSF/SBIR-STTR Award # DMI-0128081 awarded to ISOTRON. The US government has certain rights in the invention.

FIELD OF THE INVENTION

The present invention relates to a method for quickly and effectively making alumoxane nanoparticles, preferably alumina nanoparticles with surface functionalization based upon an organic carboxylic acid. The present technique makes possible the manufacture of carboxylate-alumoxane nanoparticles without requiring solvents, carrier liquids, extensive mixing times or elevated temperatures. In particular, the present invention combines a process for production of carboxylate-alumoxane nanoparticle production with the use those particles, thereby enabling many applications for which carboxylate-alumoxane nanoparticles were heretofore impossible or impractical. Such applications include coatings and related polymer compositions.

BACKGROUND OF THE INVENTION

Carboxylate alumoxanes, also known as carboxylato alumoxanes, are inorganic-organic hybrid materials that contain a boehmite-like ($[AlO(OH)]_n$) aluminum oxygen core (FIG. 1), to whose surfaces are attached covalently bound carboxylate groups (i.e., $RCO_2^-$, where R=alkyl or aryl group) (FIG. 2). The carboxylate groups are tethered to the aluminum-oxygen surface through bidentate bonding of the carboxylate group to two aluminum atoms on the surface of the boehmite particle. The properties and processability of the carboxylate alumoxanes are strongly dependent on the nature and size of the attached organic groups.

Until recently, carboxylate alumoxanes were not ideal as processable precursors because they were relatively difficult to prepare. New synthetic routes, including aqueous based techniques, have been discovered which have reduced the high cost of preparing the carboxylate alumoxanes.

Although there can be significant advantages to the synthesis of carboxylate alumoxanes via the sol-gel route (such as preparation of small particles size and good homogeneity), however, a number of significant difficulties remain. For example, while the reaction of boehmite with a carboxylic acid can be carried out in either water or a variety of organic solvents (including, but not limited to toluene and xylene), it is preferable to use water as the solvent so as to minimize the production of environmentally problematic waste. In a typical reaction, the carboxylic acids are added to boehmite or pseudoboehmite particles, the mixture is heated to reflux at temperatures as high as 100° C. for a period of time, often greater than 24 hours. The water is removed and the resulting solids are collected. As can be appreciated, this process may generate excessive waste, is time consuming, and requires elevated reaction temperatures, and typically must be performed on a batch process.

It is desirable, therefore to identify materials and processes that can be continuously used to prepare carboxylate alumoxanes using lower reaction temperatures and shorter reaction times. The process would preferably lend itself to the fabrication of a wide range of carboxylate alumoxanes with fine control over composition and particle size. The present invention provides a method of making carboxylate alumoxanes that provides these benefits and avoids many of the problems of prior art processes.

SUMMARY OF THE INVENTION

The present invention relates to methods and apparatus that can be used to prepare carboxylate alumoxanes. In a preferred embodiment, solid carboxylic acid and solid boehmite particles are mixed and subjected to shear. Even in the absence of a carrier or solvent, a reaction occurs that results in the formation of carboxylate-alumoxanes. The shear forces may be on the order of one N·m and heat may optionally be applied to the reactants.

These and other embodiments of the present invention, as well as their features and advantages, will become apparent with reference to the following detailed description.

BRIEF DESCRIPTION OF THE DRAWINGS

A better understanding of the present invention can be obtained when the following detailed description of the preferred embodiment is considered in conjunction with the following drawings, in which.

NOTATION AND NOMENCLATURE

In the following discussion and in the claims, the terms "including" and "comprising" are used in an open-ended fashion, and thus should be interpreted to mean "including, but not limited to . . . " In addition, the term "nanoparticle" is intended to encompass particles having an average diameter of less than 200 nm, and more preferably less than 20 nm. The terms "nanosol" or "nanosolution" may be used interchangeably and describe a uniformly dispersed solution containing boehmite particles. Also, the size distribution of a quantity of particles is given in terms of standard deviation or particle size range. As used herein, a "narrow size distribution" is one in which the particle size range is ±20% of the average size.

DETAILED DESCRIPTION OF THE PREFERRED EMBODIMENTS

The present invention comprises a method and apparatus in which boehmite and a carboxylic acid are reacted in a high shear mixing environment to produce carboxylate alumoxanes.

In a preferred embodiment, a mixture of boehmite or pseudoboehmite and a desired carboxylic acid is formed in a shear flow apparatus. The mixture can be a mixture of solid particles that is substantially free of liquid, can contain some amount of liquid, or can be a slurry comprising solid particles in a liquid. If liquid-containing slurry is used, the liquid can be simply a carrier liquid or can be any liquid in which the carboxylic acid is soluble, including but not limited to water, toluene, and aromatic solvents such as polyethers or glycol solvents.

Figure 1:
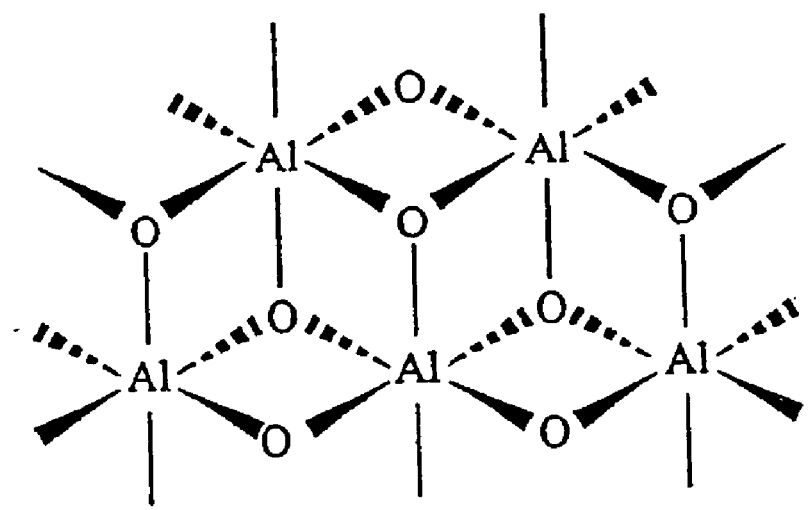
FIG. 1 is a schematic diagram showing a postulated structure for an aluminum-oxygen core structure analogous to that found in the mineral boehmite, $[Al(O)(OH)]_n$.
Figure 2:
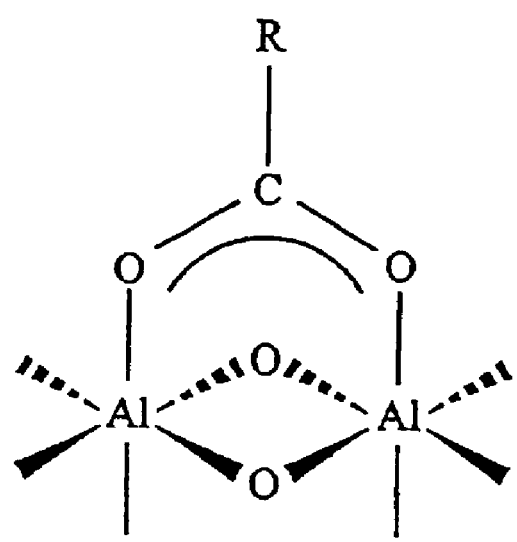
FIG. 2 is a schematic diagram showing how a carboxylate anion, $RCO_2^-$, is an isoelectronic and structural analog of the organic portion found in the siloxy-alumoxanes and is known to act as a bridging ligand across two aluminum centers.
Figure 3:
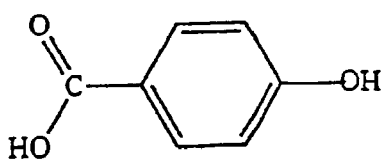
FIG. 3 is several schematic diagrams showing a representative sample of carboxylic acids suitable for reaction with boehmite or pseudoboehmite
Figure 3:
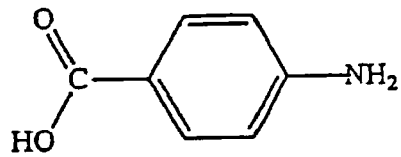
Figure 3:
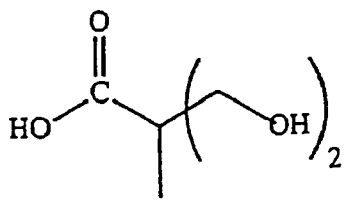
Figure 3:
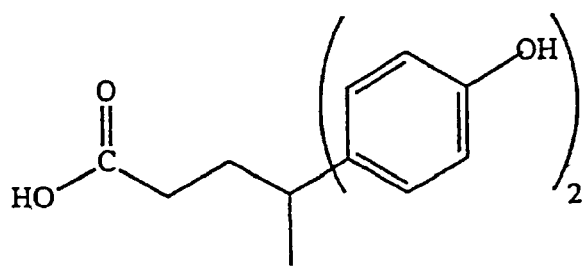
Figure 3:
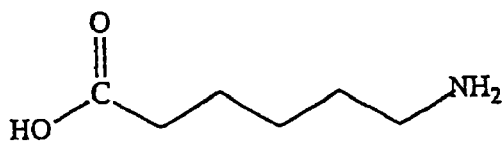
Figure 3:
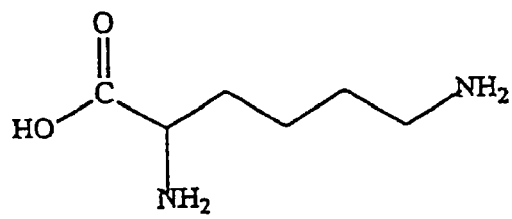

The carboxylic acid can be any monocarboxylic acid. The carboxylic acid can be aromatic or aliphatic, and can contain hetero-atom functional atoms such as nitrogen, oxygen, sulfur, etc., or hetero-atom functional groups such as amines, hydroxyls, acrylics, etc. A representative sample of suitable carboxylic acids is shown in FIG. 3.

The solubility of the carboxylate alumoxanes in a given solvent is dependent primarily on the identity of the carboxylic acid residue, which is almost unrestricted according to the present invention, providing it contains a reactive substituent that reacts with the desired co-reactants. The solubilities of the carboxylate-alumoxanes are therefore readily controllable, so as to make them compatible with any desired co-reactants.

The boehmite (or pseudoboehmite) source can be a commercial boehmite product such as Catapal (A, B, C, D, or FI, Condea-Vista Chemical Company), boehmite prepared by the precipitation of aluminum nitrate with ammonium hydroxide and then hydrothermally treated at 200° C. for 24 hours, or boehmite prepared by the hydrolysis of aluminum trialkoxides followed by hydrothermal treatment at 200° C. Preferred methods for the preparation of the pseudoboehmite or boehmite particles are those that produce particle sizes of the carboxylate alumoxanes below 1,000 nm and more preferably below 100 nm.

Figure 4:
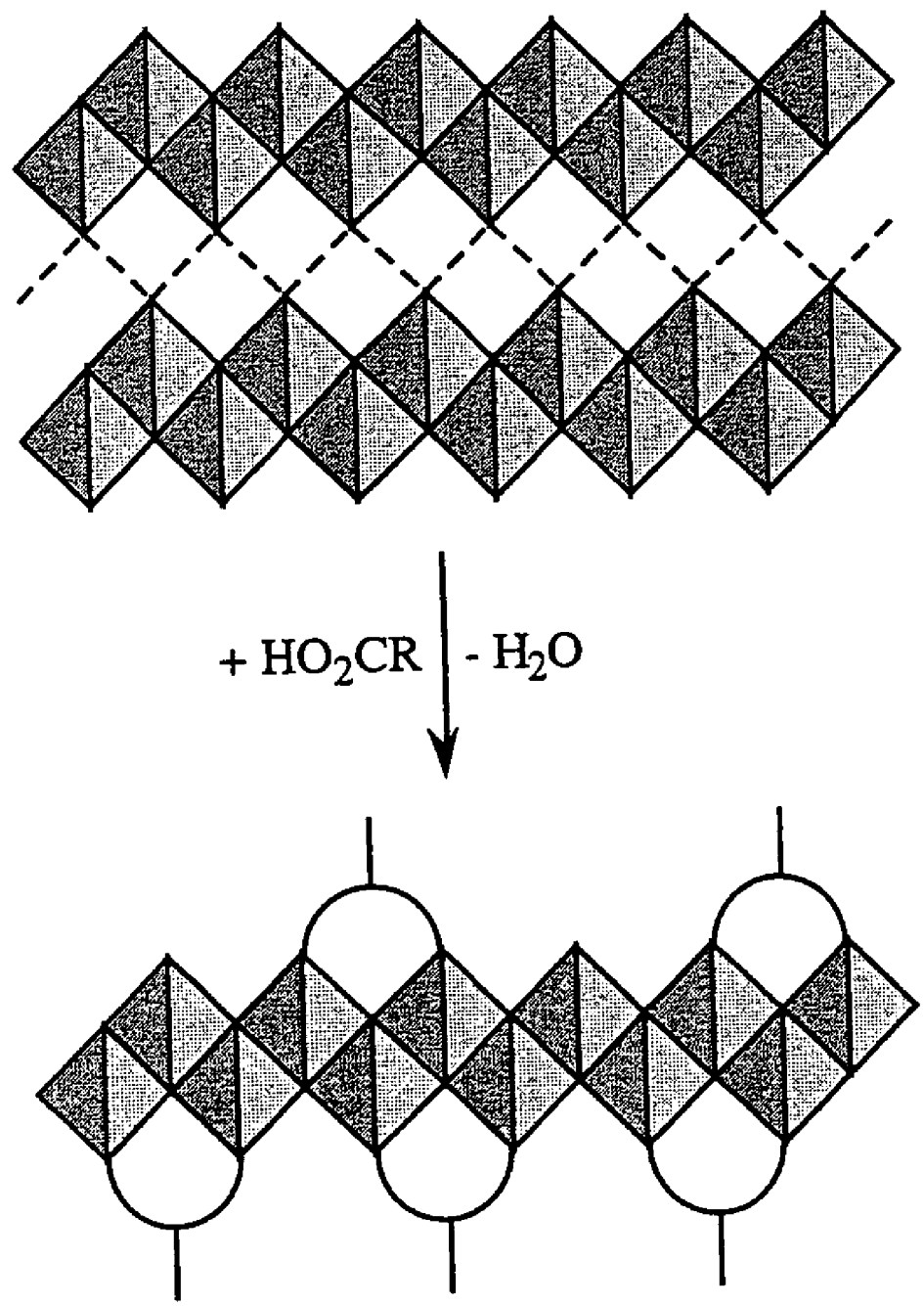
FIG. 4 is a schematic diagram showing a representation of the reaction of boehmite with carboxylic acids.

According to the present invention, the mixture of boehmite and carboxylic acid particles is subjected to high shear stresses and, preferably, elevated temperature that cause the boehmite to react with the carboxylic acid to enhance the formation of carboxylated alumoxane particles, as shown in FIG. 4. In FIG. 4, the shaded triangles represent a side view of boehmite and the carboxylate groups are represented by a semicircle and bar. The reaction shown in FIG. 4 may be a condensation reaction, wherein, for example, the carboxylic acids react with the boehmite structure, producing water as a bi-product. One embodiment of the invention entails blending the boehmite and carboxylic acid particles in a high-shear mixer. High shear mixers are known in the art and are commercially available. Such mixers are available as batch mixers or as in-line mixers and can be configured to process either mixtures of solid particles or liquid-based slurries, or both.

In embodiments in which liquid slurry is used, another apparatus that has been found to be effective for achieving the desired reactions comprises a small diameter tube, preferably having a predetermined length. The diameter of tube is preferably small enough and the viscosity and rate of flow of the slurry are such that particles in the slurry undergo high shear as they pass through the tube.

In some embodiments, the shearing apparatus may include a rotor/stator device or other mechanical shearing means including the addition of conventional materials that help with the exfoliation of the boehmite by increasing the viscosity of the slurry. For example, a ceramic medium in the range of 5 to 1,000 microns can be used. Examples include ceramic microspheres, micaceous iron oxide, mica, and so forth.

As an example of a liquid/solid phase reaction, it has been found that a premixed slurry, or nanosol, of boehmite particles having an average size in the range of microns and carried in a liquid comprising 70–97 wt. % of water and 3–30 wt. % of a carboxylic acid, when fed through the small diameter tube at a rate in the range of one tube volume per minute, is converted into carboxylate alumoxane nanoparticles after making a single pass in the pipe. In a preferred embodiment, high shear is realized at velocities above about 1,000 ft/min, more preferably above about 5,000 ft/min, and more preferably in the range of 7,000–9,000 ft/min. A preferred flow rate has been found to be between 5,000 and 9,000 ft/min.

In some embodiments, the processing system may further include a heat source. The heat source may comprise any external heat mechanism including, but not limited to an electric heater. Alternatively, at least a portion of the heat source can result from the mechanical energy that is applied via the mechanical shearing means.

In a preferred embodiment, the apparatus comprises a rheometer or rheomixer, such as are commercially available from various companies, including Thermo Haake, Thermo Electron (Karlsruhe) GmbH, Dieselstrasse 4, Karlsruhe, BW 76227, Germany. As can be appreciated, rheometers or rheomixers have internal mixing chambers in which high shear stresses are created, thereby exposing the agglomerates in a mixture to shear forces that will tend to break up the agglomerates. The mixing is generally achieved via blades. Heaters may be present to keep the mixture at a predetermined viscosity/rheology. The "Examples" section below details samples prepared using a Haake Rheomixer 600 instrument having roller-style blades or rotors.

Carboxylate alumoxane nanoparticles formed using the present method have an average diameter of less than 200 nm, and more preferably less than 20 nm. Furthermore, the nanoparticles exhibit a narrow particle size distribution, wherein any individual particle size typically is ±20% of the average nanoparticle size.

The present inventors have discovered that the application of shear, and in some instances the combination of high shear and a high viscosity nanosol mixture, greatly accelerates the formation of carboxylate alumoxane nanoparticles and results in a composition in which the boehmite is quickly exfoliated to yield a composition having a narrow particle size distribution. Without wishing to be bound by any particular theory, it is believed that the cleavage of the boehmite is accomplished by shear forces applied to the particles as they pass through the shear mixer, or by a combination of shear forces and heat. As described above, at least a portion of the heat may result from the mechanical energy that is applied during shearing. The heat may drive the reaction between the boehmite and the carboxylate groups. The shear may promote the physical interaction between the boehmite and the carboxylate groups, effectively exposing reaction sites of the two reactants.

The present technique can achieve in minutes a particle size reduction that requires more than 24 hours using the conventional technique. Because the formation of carboxylate alumoxane nanoparticles can now be achieved very quickly, the process can readily be carried out in a continuous mode.

EXAMPLES

A Haake Rheomixer 600 instrument was used for all experiments. The miniaturized internal mixer (MIM) was developed for formulating multi-component polymer systems and studying flow behavior, thermal sensitivity, and shear sensitivity. Since torque is proportional to shear stress and rpm to shear rate, shear sensitivity, viscosity and the energy required to process a material can be obtained. The Rheomixer consists of three independent sections, each heated and controlled by its own heater and temperature controller. The mixing chamber is shaped like a figure eight, with a rotor in each chamber. The mixing rotors revolve in opposite directions and at different controlled speeds, to achieve shear action. MIMs have two characteristic geometric features; they have a narrow a gap between the rotor wings and the mixer wall and a larger space between the rotors. The rotors rotate typically at a relative speed of 3:2; the left rotor rotates clockwise while the right one counter clockwise in order to affect a shearing action on the mixture. The mixture is sheared repeatedly through the narrow gap and recycled to the core of the mixture between the rotors. The rotors themselves have helical projections that perform additional axial mixing by moving the mixture around the rotor and towards the center. Extensive mixing takes place exclusively in the core of the mixture while dispersion occurs in the vicinity of the narrow gap under the rotor wing, in which high shear stresses are created exposing the agglomerates to hydrodynamic forces that will tend to break up the agglomerates. It will be understood that the foregoing equipment is exemplary only and that other mix or shearing equipment could be used.

The Haake Rheomixer 600 instrument was preset with the following settings prior to mixing carboxylic acid and boehmite: (1) the heaters were allowed to reach the desired temperature; and (2) after the heaters were set, the roller-style rotors were brought to the desired speed or rate per minute (rpm).

Figure 5:
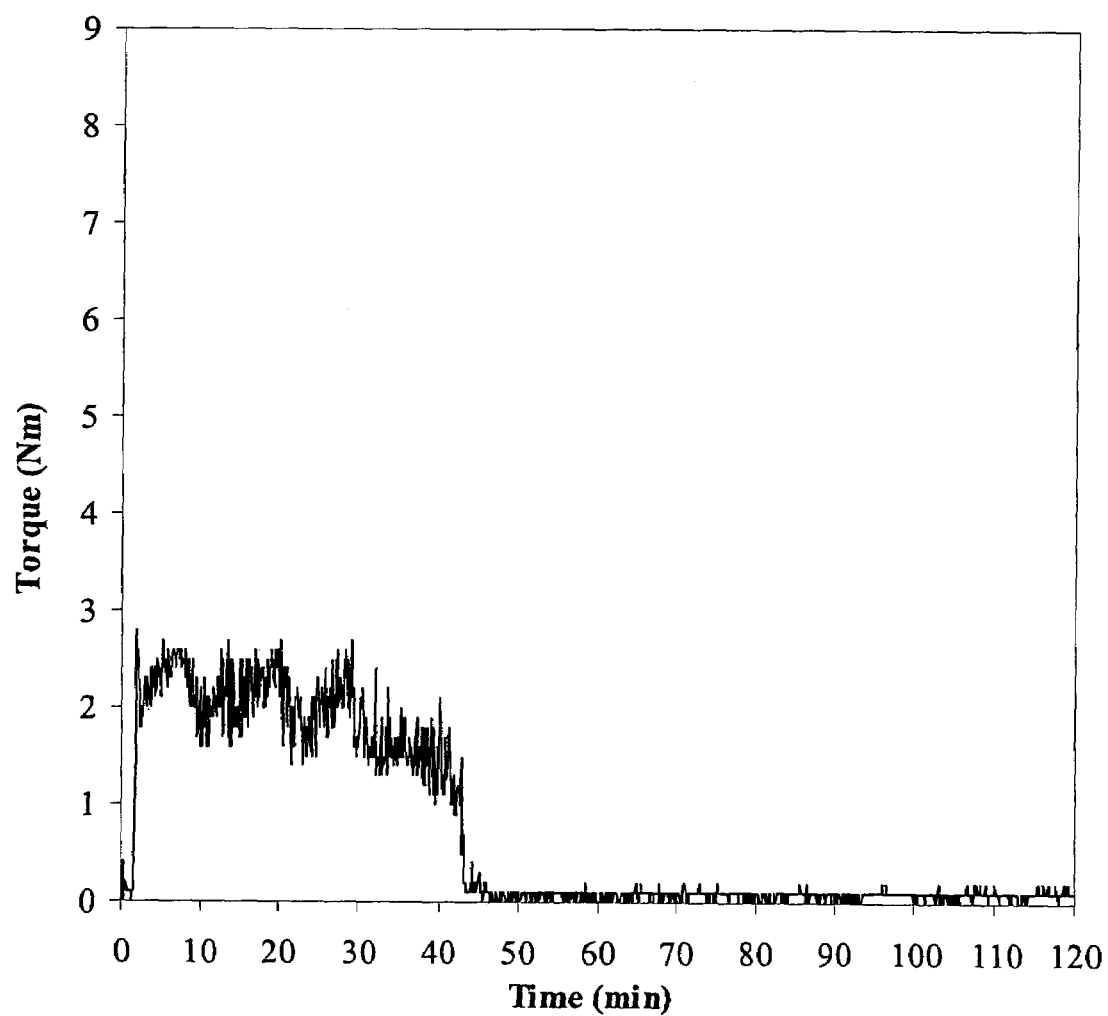
FIG. 5 is an Exemplary plot of calculated torque vs. reaction time for a batch reaction carried out in accordance with the principles of the present invention.

A sample of a carboxylic acid (L-lysine (14 g)) and boehmite (6.0 g) was then added to the rheomixer. In each case, the experiment was allowed to run for 120 minutes. In many instances, however, it appeared that the reaction had reached completion well before the end of the 120 minute period. Completion of the reaction was indicated by a significant drop in both torque and temperature. Because torque is proportional to shear stress and rpm is proportional to shear rate, shear sensitivity, viscosity and the energy required to process the material could be calculated. Accordingly, the "time to complete" was determined from the calculated torque versus reaction time plot. FIG. 5 is an exemplary plot and corresponds to Example C.

After 120 minutes, the sample was extracted into water and any unreacted boehmite was separated. The solution was then pumped dry or the product precipitated with ethanol. The resulting white solid was air-dried. This sample preparation was repeated a number of times to yield the data in Table 1, with each of the samples having essentially the same initial reactants. Referring to Table 1, particle size measurements were obtained on a Coulter N4 Plus Particle Size Analyzer at an angle of 90° and a concentration of 1.0 g.L$^{-1}$. The water used for dispersing the alumoxanes was distilled and filtered (using a 0.2 μm filter) prior to use.

TABLE 1

| Run | Temp (° C.) | Rpm | Average Size (nm) | Time to Complete (min) |
|---|---|---|---|---|
| A | 60 | 60 | 1684 | >120 |
| B | 70 | 60 | 200 | >120 |
| C | 80 | 60 | 3.2 | 43 |
| D | 90 | 60 | 1.92 | 0.7 |
| F | 110 | 60 | 2.02 | 38 |
| H | 130 | 60 | 1.54 | 12 |
| I | 110 | 70 | 1.13 | 11 |
| J | 110 | 80 | 1.48 | 40 |

Referring to Table 1, it is believed that the combination of increasing temperature and increasing shear rate generally leads to smaller particle size. For example, at temperatures of 80° C. and above, the average particle size decreases dramatically. Also, as shown in Examples I and J, the increase in shear rate (rpm) may aid in the production of smaller particles. In accordance with the spirit of the present invention, temperature and shear conditions which produce particles having an average size of less than 100, more preferably less than 20, more preferably less than 50 nm and still more preferably less than 2 nm are preferred. Furthermore, in some embodiments, while any particle shape may be produced, particles having a generally round or oval shape are preferred.

From the foregoing experiments, it was determined that, in order to achieve the desired rapid reaction, the torque applied by the mixer is preferably at least 1 N·m, more preferably at least 2 N·m, and still more preferably at least 3 N·m. Nonetheless, shear rates as low as 0.2 or 0.5 N·m may be sufficient, particularly if additives are used to enhance the reaction. If the shear rates greater than 1 N·m are combined with elevated temperatures of at least 60° C., more preferably at least 70° C., more preferably at least 80° C., more preferably at least 90° C., and still more preferably at least 100° C., the reaction time can be reduced to mere minutes. In accordance with the spirit of the present invention, temperature and shear conditions which produce desirable particles having a reaction time (time of completion) of less than 2 hours, more preferably less than 1 hour, more preferably less than 30 minutes and still more preferably less than 10 minutes are preferred.

Uses

One traditional approach to the use of nanoparticles in industrial applications is to manufacture and sell the nanoparticles as a "drop-in" additive. Because nanoparticles are not created on-site, there is little flexibility in the conventional approach. The prior art processes are disadvantageous for commercial use because, as mentioned above, such a process poses a logistical problem, which in turn increases costs.

The present method allows carboxylate-alumoxane nanoparticles to be generated in situ, using mixing equipment that is readily available in most coating manufacturing facilities. In many instances, unlike the prior art technique, the present technique avoids need to recover and wash the carboxylate-alumoxane nanoparticles. In addition, because the present method allows processing to take place in minutes or hours instead of days it is much better suited to use in conjunction with a commercial coating manufacturing facility or other commercial/industrial application, such as packaging film production units or adhesive manufacturing plants.

It is expected that the present invention will have a broad and significant impact on the industrial coatings market; which includes interior linings, chemical resistant coatings, and rail car linings. One example of a potential use for carboxylate-alumoxane nanoparticles is a highly flexible and impermeable polyurea nanoparticle composite coating that is suitable for many applications; for example, on the many bridges that are protected with red-lead coatings. Overcoating with this polyurea-nanocomposite could extend service life without the prohibitively expensive removal of the old coating.

Polyurea polymers offer many excellent protective coating properties, such as flexibility over a wide temperature range, adherence to most substrates, low stress to an "under-coat", allowing for its use as a restorative overcoat. In addition, they can bridge cracks, which is an important consideration in protecting concrete structures. Over the past decade polyureas have grown in popularity and are becoming one of the more promising of the modern coatings and sealants, but their permeability to oxygen and water vapor compromises their corrosion inhibition.

The preferred function ligands have primary acid sites. In such cases, the carboxylate-alumoxane nanoparticles react with polyurea precursor molecules, i.e. the isocyanate species, to yield a polymer having enhanced resistance to oxygen and water diffusion and increased tensile strength. Suitable polyurea precursors for use in this embodiment include isophorone di-isocyanate (IPDL), methylene bis phenyl di-isocyanate (MDI), and toluene di-isocyanate (TDI).

In one embodiment, the carboxylate-alumoxane nanoparticles are formed in a high-shear device that is upstream of a mixing device. In the mixing device, the newly-formed carboxylate-alumoxane nanoparticles are mixed with a desired second material. The second material can be a coating, such as a paint or polymeric coating, a moldable composition, such as a polyurea, or an epoxy polymer. The ability to make carboxylate-alumoxane nanoparticles in a high shear mixing environment at their site of use will greatly simplify their use and application by unskilled operators. In addition, the ability to make carboxylate-alumoxane nanoparticles at point of use will simplify shipping and cut out one potential step of manufacturing, and thus cost of production of coatings or other articles prepared using the alumoxanes.

The present apparatus for mixing the boehmite and the carboxylic acid can be either suitable for a chemical plant and have the potential for large scale continuous processing or as a hand held/back-pack style reactor for use by an individual.

While the present invention has been disclosed and described in terms of the formation of carboxylated alumoxane particles in a solid phase or slurry reaction, it will be understood that the principles disclosed herein may be altered or modified with deviating from the scope of the invention. For example, shear could be applied via any suitable means. Accordingly, the scope of protection is not limited by the description set out above, but is limited only by the claims that follow, that scope including all equivalents of the subject matter of the claims. Each and every claim is incorporated into the specification as an embodiment of the present invention. Thus the claims are a further description and are an addition to the preferred embodiments of the present invention. Use of the term "optionally" with respect to any element of a claim is intended to mean that the subject element may or may not be present. Both alternatives are intended to be within the scope of the claim.

Finally, the discussion of a reference in the Background is not an admission that it is prior art to the present invention, especially any reference that may have a publication date after the priority date of this application.

We claim:

1. A method for forming carboxylate-alumoxane nanoparticles, comprising:
    subjecting a mixture comprising boehmite and carboxylic acid to mechanical shear in the substantial absence of a solvent.

2. The method according to claim 1 wherein the method is carried out at a temperature above ambient.

3. The method according to claim 1 wherein the method is carried out at a temperature greater than 80° C.

4. The method according to claim 1 wherein the method is carried out substantially in the absence of a liquid phase.

5. The method according to claim 1 wherein the carboxylate-alumoxane particles are formed within two hours of initiation of shear application.

6. The method according to claim 1 wherein the carboxylate-alumoxane particles are formed within one hour of initiation of shear application.

7. The method according to claim 1 wherein the mixture is heated by the application of heat from an external source.

8. The method according to claim 1 wherein the carboxylic acid is selected from the group consisting of an aliphatic carboxylic acid, an aromatic carboxylic acid, and a carboxylic acid containing an additional chemically reactive functional group.

9. The method according to claim 1 wherein the mixture is subjected to mechanical shear by passing it through a tube at a linear velocity of at least about 1,000 ft/min.

10. The method according to claim 1 wherein the mixture is subjected to mechanical shear by passing it through a device comprising a rotor and a stator.

11. The method according to claim 1 wherein the carboxylate-alumoxane nanoparticles have an average size of less than 200 nm.

12. The method according to claim 1 wherein the carboxylate-alumoxane nanoparticles have a size distribution such that the particle size range is ±20% of the average size.

13. The method according to claim 1 wherein the method is carried out at a temperature greater than 80° C. and the carboxylate-alumoxane particles are formed within two hours of initiation of shear application.

14. The method according to claim 13 wherein the carboxylate-alumoxane particles are formed within 30 minutes of initiation of shear application.

* * * * *